United States Patent [19]

Neuworth

[11] 3,956,359
[45] May 11, 1976

[54] ALKYLIDENEDITHIOBISPHENOLS

[75] Inventor: Martin B. Neuworth, Trumbull, Conn.

[73] Assignee: Continental Oil Company, Ponca City, Okla.

[22] Filed: Nov. 20, 1974

[21] Appl. No.: 525,330

Related U.S. Application Data

[60] Division of Ser. No. 367,055, May 29, 1973, Pat. No. 3,897,500, which is a division of Ser. No. 206,929, Dec. 10, 1971, Pat. No. 3,786,100, which is a division of Ser. No. 835,811, June 23, 1969, abandoned, which is a continuation-in-part of Ser. Nos. 637,622, May 11, 1967, abandoned, and Ser. No. 637,649, May 11, 1967, abandoned, and Ser. No. 637,650, May 11, 1967, abandoned.

[52] U.S. Cl. .............................................. 260/470
[51] Int. Cl.² ..................................... C07C 149/40
[58] Field of Search ................................... 260/470

[56] References Cited

UNITED STATES PATENTS 3,576,883  4/1971  Neuworth .......................... 424/337

Primary Examiner—Howard T. Mars
Attorney, Agent, or Firm—Cortlan R. Schupbach, Jr.

[57] ABSTRACT

Compounds having the general formula:

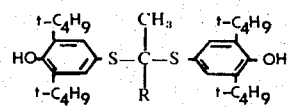

where R is an alkyl radical substituted by a radical selected from the class consisting of alkoxy, carbonyl and ester radicals. The compounds are useful for reducing blood cholesterol in warm-blooded animals.

2 Claims, No Drawings

ALKYLIDENEDITHIOBISPHENOLS

CROSS-REFERENCE TO RELATED APPLICATION

This is a division of application Ser. No. 367,055, filed May 29, 1973, now U.S. Pat. No. 3,897,500 which in turn was a division of application Ser. No. 206,929, filed Dec. 10, 1971 (now U.S. Pat. No. 3,786,100), which in turn was a division of application Ser. No. 835,811, filed June 23, 1969 (now abandoned), which in turn was a continuation in part of applications Ser. Nos. 637,622, 637,649 and 637,650, all filed May 11, 1967 (all now abandoned).

BACKGROUND OF THE INVENTION

1. Field of the Invention

This invention relates to a new and useful group of sulfur-containing bisphenols.

2. Description of the Prior Art

U.S. Pat. Nos. 2,278,224 and 2,472,318 describe compounds defined by the formula DRxR'xRD, in which R is an aryl or alkyl aryl, or a substituted aryl or alkyl aryl group, x is a sulfur, oxygen or tellurium, but preferably a sulfur group, R' is an alkyl or substituted alkyl group and D is an inhibitor group taken from the class of hydroxy, amino, sulfide, disulfide, or polysulfide groups.

SUMMARY OF THE INVENTION

The novel chemical compounds of the present invention possess the property of lowering the cholesterol content of the blood of warm-blooded animals. They have the following general formula:

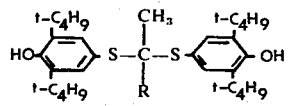

where R is an alkyl radical substituted by a radical selected from the class consisting of alkoxy, carbonyl and ester radicals.

The compounds of the present invention are prepared as follows. The appropriate 4-mercaptophenol is reacted with the appropriate carbonyl compound in the presence of a strong acid catalyst according to the following equation:

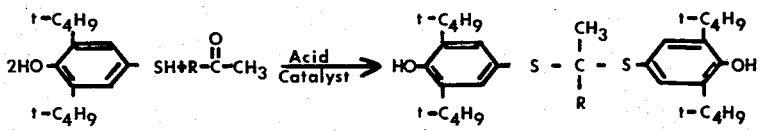

where R is an alkyl radical substituted by a radical selected from the class consisting of alkoxy, carbonyl and ester radicals. The appropriate 4-mercaptophenol may be prepared by any one of several known methods. For example, thiocyanation of the appropriate phenol, followed by reduction, is one of such methods. For details, see Organic Reactions, Vol. III, Chapter 6, by Roger Adams et al.; also the article by Muller et al., entitled "Untersuchungen an schwefelhaltigen Aroylen mittels der Electronenresonanz" in Liebig's Annalen (1961, Bd. 645, p. 79); and, finally, U.S. Pat. No. 3,129,262.

The mercaptophenol and the appropriate carbonyl compound are preferably dissolved in an inert organic solvent to provide a homogeneous reaction mixture. At least a stoichiometric amount of the carbonyl compound is used. The catalyst is a strong acid catalyst, for example hydrochloric acid, sulfuric acid, perchloric acid, and strong acid cationic exchange resins. The reaction is mildly exothermic initially; external heating is then required to maintain the reaction temperature, generally between 50° and 100°C. Reaction times of 0.8 to 6 hours are generally required.

The following examples illustrate the compounds of this invention. In each example, the chemical name and structural formula of the compound are first given. The identity of the compound produced in each example was established by conventional methods of analysis.

EXAMPLE 1

Preparation of:
2,4-Pentanedione:2,2-bis(3,5-di-t-butyl-4-hydroxyphenyl)mercaptal

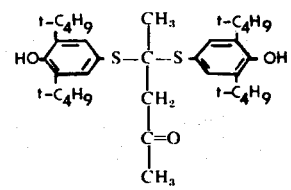

A 500-milliliter flask (stirrer, thermometer, condenser) was charged with 23.8 grams of 2,6-di-t-butyl-4-mercaptophenol (0.1 mole) and 5.0 grams of 2,4-pentanedione (0.05 mole) in 150 milliliters of methanol. 8.6 Milliliters of 12N HCl was added, and the mixture held at about 60°–70°C. for about three hours. The product mixture was placed in a separatory funnel to which 100 milliliters of hexane and 200 milliliters of H₂O were added. The aqueous phase was drained. A solid product was recovered from the hexane solution by partial stripping of the solvent. The solid was recrystallized from 95% ethanol (USP). It weighed 15.6 grams and had a melting point of 126°–130°C.

EXAMPLE 2

Preparation of:
2,4-Pentanedione:2,2-bis(3,5-di-t-butyl-4-hydroxyphenyl)mercaptal, 4,4-diethylacetal

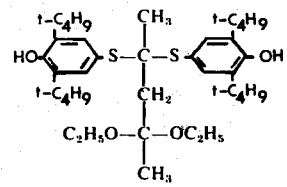

A 500-milliliter flask (stirrer, thermometer, condenser with H₂O scrubber, gas inlet) was charged with 47.6 grams of 2,6-di-t-butyl-4-mercaptophenol (0.2 mole) and 5.0 grams of pentanedione (0.05 mole) in 166 milliliters of anhydrous ethyl ether. The solution was saturated with dry gaseous HCl, and maintained at about 80°C. for about 30 minutes. The product was placed in a flask and stripped of most of the solvent under H₂O pump vacuum with moderate heating. A heavy oil precipitated. 70 Milliliters of benzene was added to the flask and the resultant solution was placed in a separatory funnel and washed with 100 milliliters of H₂O. The organic phase was then washed with two 100-milliliter portions of 5% caustic solution. The caustic fraction was drained off. The benzene phase was stripped of benzene by a water aspirator vacuum. A viscous oil formed which was dissolved in 40 milliliters of hexane and then cooled in a dry ice chest. A crystalline product was obtained which was filtered on chilled equipment; washed with very cold hexane; and dried in a vacuum desiccator. It weighed 8.8 grams and had a melting point of 96°–105°C. This was recrystallized from 20 milliliters of ethanol; filtered; washed with ethanol; and dried in a vacuum desiccator (38°C.). Its weight was 5.2 grams and its melting point was 120°–122.5°C.

EXAMPLE 3

Preparation of: 2-Octanone: bis(3,5-di-t-butyl-4-hydroxyphenyl)mercaptal

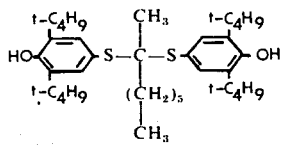

A 500-milliliter flask (stirrer, thermometer, condenser with H₂O scrubber, gas inlet) was charged with 23.8 grams of 2,6-di-t-butyl-4-mercaptophenol (0.1 mole) and 6.4 grams of 2-octanone (0.05 mole) (the stoichiometric amount was used rather than the usual 100% excess because of the difficulty of removing the unused ketone from the reaction mixture), in 150 milliliters of methanol. The charge was heated to about 50°C., saturated with gaseous HCl, and held at 68°C. for about 6 hours. A crystalline precipitate formed. The product mixture was filtered, washed with 100 milliliters 90% MeOH and air dried. It weighed 27.3 grams and had a melting point of 126°–127°C. The yield was 90%.

EXAMPLE 4

Preparation of: Acetoacetic Acid: 3 thio, ethyl ester; bis(3,5-di-t-butyl-4-hydroxyphenyl)mercaptal

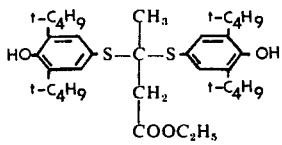

A 500-milliliter flask (stirrer, thermometer, condenser, sparge tube, heating mantle) was charged with 47.6 grams of 3,5-di-t-butyl-4-hydroxythiophenol, 13.0 grams of ethyl acetoacetate, and 150 milliliters of anhydrous ethanol. The mixture was saturated with HCl gas. In 3 minutes the temperature rose from 19° to 74°C.; was held at reflux 2 hours; cooled; and diluted with 50 milliliters water to precipitate a heavy white paste. The paste was taken up in 100 milliliters benzene and 100 milliliters chloroform; washed to neutrality with three 100-milliliter portions of water; and dried over MgSO₄. The mixture was filtered and the benzene distilled off to yield a yellow viscous oil which crystallized upon standing. 25.4 Grams of product were recovered having a melting point of 104° to 108°C. The yield was 43 percent.

EXAMPLE 5

Preparation of: 2-Pentanone: 4-methyl, bis(3,5-di-t-butyl-4-hydroxyphenyl) mercaptal

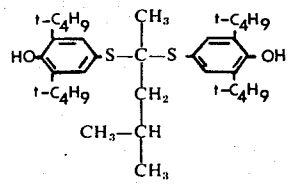

A 500-milliliter flask (stirrer, thermometer, condenser with H₂O scrubber, gas inlet) was charged with 23.8 grams of 2,6-di-t-butyl-4-mercaptophenol (0.1 mole) and 10.0 grams of methyl isobutyl ketone (0.1 mole) in 150 milliliters methanol. The solution was heated to about 50°C. and saturated with HCl. The mixture was held at a temperature near 70°C. for about 6 hours. A crystalline solid had formed in the flask. The mixture was filtered; washed with 100 milliliters of 90% methanol; and dried. 12.8 Grams of product were recovered having a melting point of 126°–130°C. The yield was 44 percent.

EXAMPLE 6

Preparation of: Pyruvic Acid: 2-thio, ethyl ester, bis(3,5-di-t-butyl-4-hydroxyphenyl)mercaptal

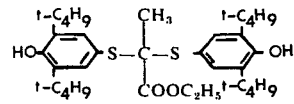

A 500-milliliter flask (stirrer, thermometer, sparge tube, condenser, heating mantle) was charged with 47.6 grams of 2,6-di-t-butyl-4-mercaptophenol, 11.6 grams of ethyl pyruvate, and 150 milliliters of anhydrous denatured ethanol. The mixture was warmed to 35°C. to aid in dissolving the large chunks of mercaptophenol. Then, HCl gas was introduced (in 3 minutes, the temperature rose from 35°C. to 66°C.), and the solution was refluxed for 2 hours. The mixture was diluted with 200 milliliters of water and extracted with 100, then 50, milliliters of benzene. The combined benzene phases were washed to neutrality with three 100-milliliter portions of water, and dried over MgSO₄. The mixture was filtered and stripped of benzene to yield a yellow solid precipitate. 33.9 Grams of white solid were recovered which had a melting point of 117° to 118°C.

The compounds of the present invention are useful for reducing the level of cholesterol in the blood of warm-blooded animals. They may be employed directly in suitable dosage, or as the active ingredient in a feed composition, or with suitable nontoxic carriers. Good results are obtained with dosages of from 15 to 600 milligrams of active compound per kilogram of body weight of the recipient to provide a total intake of up to 3000 mg/kg per 24 hours.

The following table tabulates the percent reduction of cholesterol in the blood of rodents effected by the use of compounds of this invention. The compound was added to commercial rodent chow at a level of 0.125% by weight, and the mice were allowed to feed ad libitum for two weeks. At the end of this period, serum cholesterol determinations were performed on all the mice.

TABLE I

| Compound | Percent Reduction |
|---|---|
| Example 1 | |
| 2,4-Pentanedione:2,2-Bis-(3,5-di-t-butyl-4-hydroxyphenyl)-mercaptal | 46 |
| Example 2 | |
| 2,4-Pentanedione:2,2-Bis-(3,5-di-t-butyl-4-hydroxyphenyl) mercaptal-4,4-diethyl acetal | 58 |
| Example 3 | |
| 2-Octanone:Bis-(3,5-di-t-butyl-4-hydroxyphenyl)-mercaptal | 17 |
| Example 4 | |
| Acetoacetic Acid:3-Thio, ethyl ester, Bis-(3,5-di-t-butyl 4-hydroxyphenyl)-mercaptal | 51 |
| Example 5 | |
| 2-Pentanone: 4-methyl-Bis-(3,5-di-t-butyl-4-hydroxyphenyl)-mercaptal | 21 |
| Example 6 | |
| Pyruvic Acid: 2-Thio, ethyl ester, Bis-(3,5-di-t-butyl-4-hydroxyphenyl)-mercaptal | 24 |

The percent reductions in cholesterol content set forth in the foregoing Table I were calculated from statistically significant data. The general procedure was as follows:

Separate portions of balanced rodent mash were mixed together with each test compound to prepare a series of separate compositions each containing 0.125 percent by weight of one test compound. Separate groups of male mice of the same origin and past history were fed for two weeks on separate diets consisting of one of the above-described compositions. Based on observations of average consumption of the composition and the concentration of the test compound, each mouse received an estimated oral dosage of about 250 milligrams of test compound per kilogram of animal body weight per day. A separate group of similar male mice was fed for two weeks on a diet consisting of an identical rodent mash which contained no test compound to serve as a check. At the end of the two-week period, the mice in each group were anesthetized with ether and exsanguinated.

Serum cholesterol levels were determined for each mouse by taking a 0.05 milliliter aliquot of serum from each mouse and adding to the aliquot 3 milliliters of a 0.08 percent solution of ferric chloride in pure acetic acid. The serum was mixed with the ferric chloride-acetic acid solution and the mixture was allowed to stand for 10 to 15 minutes to flocculate protein. The protein was precipitated by centrifugation and the clear supernatent fluid was transferred to a stoppered test tube. Two milliliters of sulfuric acid was added to the supernatant and mixed well. The tubes were then left to stand exposed to air for 20 to 30 minutes. Serum cholesterol was determined by measuring the percent transmission at a wave length of 560 millimicrons in a spectrophotometer and comparing the percent transmission to that observed with solutions containing known amounts of cholesterol.

The average serum cholesterol level in milligrams of cholesterol per 100 milliliters of serum was calculated for each test group and for the check group. The percentage reduction in serum cholesterol level was calculated by dividing the difference between the cholesterol levels in the test group and the check group by the cholesterol level in the check group and multiplying the quotient by 100.

According to the provisions of the patent statutes, I have explained the principle, preferred construction, and mode of operation of my invention and have illustrated and described what I now consider to represent its best embodiment. However, I desire to have it understood that, within the scope of the appended claims, the invention may be practiced otherwise than as specifically illustrated and described.

I claim:

1. Acetoacetic Acid:3-Thio, ethyl ester-Bis-(3,5-di-t-butyl-4-hydroxyphenyl)-mercaptal.

2. Pyruvic Acid: 2-Thio, ethyl ester-Bis-(3,5-di-t-butyl-4-hydroxyphenyl)-mercaptal.

* * * * *